(12) United States Patent
Tashiro

(10) Patent No.: US 10,105,124 B2
(45) Date of Patent: Oct. 23, 2018

(54) ULTRASOUND DIAGNOSTIC EQUIPMENT WITH RECHARGEABLE ULTRASOUND PROBES

(71) Applicant: FUJIFILM CORPORATION, Tokyo (JP)

(72) Inventor: Rika Tashiro, Ashigarakami-gun (JP)

(73) Assignee: FUJIFILM CORPORATION, Tokyo (JP)

( * ) Notice: Subject to any disclaimer, the term of this patent is extended or adjusted under 35 U.S.C. 154(b) by 302 days.

(21) Appl. No.: 13/773,876

(22) Filed: Feb. 22, 2013

(65) Prior Publication Data

US 2013/0165796 A1    Jun. 27, 2013

Related U.S. Application Data

(63) Continuation of application No. PCT/JP2011/070267, filed on Sep. 6, 2011.

(30) Foreign Application Priority Data

Sep. 10, 2010   (JP) .................................. 2010-203121
Aug. 31, 2011   (JP) .................................. 2011-188838

(51) Int. Cl.
*A61B 8/00*          (2006.01)
*A61B 8/08*          (2006.01)
(Continued)

(52) U.S. Cl.
CPC ................ *A61B 8/56* (2013.01); *A61B 8/145* (2013.01); *A61B 8/4433* (2013.01);
(Continued)

(58) Field of Classification Search
CPC ......... A61B 8/4433; A61B 8/56; A61B 8/145; A61B 8/4472; A61B 8/4477;
(Continued)

(56) References Cited

U.S. PATENT DOCUMENTS 5,349,281 A * 9/1994 Bugaj ............................ 320/160
5,357,187 A * 10/1994 Park .............................. 320/116
(Continued)

FOREIGN PATENT DOCUMENTS

| JP | 2002-223529 A | 8/2002 |
|---|---|---|
| JP | 2002-238177 A | 8/2002 |
| JP | 2003-010177 | 1/2003 |

OTHER PUBLICATIONS

Chinese Office Action dated Jul. 2, 2014 with an English translation thereof.
(Continued)

*Primary Examiner* — Amelie R Gillman
(74) *Attorney, Agent, or Firm* — McGinn I.P Law Group, PLLC.

(57) ABSTRACT

An ultrasound diagnostic equipment has at least one rechargeable ultrasound probe with a built-in battery, and a diagnostic equipment body connected to the at least one ultrasound probe in a wireless manner, wherein the diagnostic equipment body includes a power supply unit which supplies power to the battery of the at least one ultrasound probe, and a power supply controller which causes the battery of the at least one ultrasound probe to selectively perform refresh charging and top-up charging using the power supply unit on the basis of power supply information to the battery of the at least one ultrasound probe and the examination situation in the diagnostic equipment body.

4 Claims, 4 Drawing Sheets

(51) Int. Cl.
*A61B 8/14* (2006.01)
*H01M 10/44* (2006.01)
*H01M 10/46* (2006.01)

(52) U.S. Cl.
CPC .......... *A61B 8/4472* (2013.01); *A61B 8/4477* (2013.01); *A61B 8/4488* (2013.01); *A61B 8/462* (2013.01); *A61B 8/467* (2013.01); *A61B 8/5207* (2013.01); *A61B 8/54* (2013.01); *H01M 10/44* (2013.01); *H01M 10/46* (2013.01)

(58) Field of Classification Search
CPC ....... A61B 8/4488; A61B 8/462; A61B 8/467; A61B 8/5207; A61B 8/54; H01M 10/44; H01M 10/46
See application file for complete search history.

(56) References Cited

U.S. PATENT DOCUMENTS

| | | | | |
|---|---|---|---|---|
| 5,640,079 | A * | 6/1997 | Nelson | H01M 10/44 320/153 |
| 5,754,029 | A * | 5/1998 | Mann et al. | 320/106 |
| 5,793,188 | A * | 8/1998 | Cimbal et al. | 320/130 |
| 5,942,878 | A | 8/1999 | Ito | |
| 6,271,643 | B1 * | 8/2001 | Becker | H02J 9/061 320/112 |
| 6,664,757 | B1 * | 12/2003 | Gauthier | H01M 10/46 320/103 |
| 6,741,065 | B1 | 5/2004 | Ishii et al. | |
| 8,154,244 | B1 * | 4/2012 | Gorham et al. | 320/103 |
| 2003/0169017 | A1 * | 9/2003 | Ariga | H02J 7/0073 320/125 |
| 2004/0059527 | A1 * | 3/2004 | Kobayashi | G06F 1/26 702/63 |
| 2004/0179332 | A1 * | 9/2004 | Smith et al. | 361/681 |
| 2006/0103352 | A1 | 5/2006 | Jones | |
| 2008/0194961 | A1 * | 8/2008 | Randall | A61B 8/00 600/459 |
| 2009/0096419 | A1 * | 4/2009 | White et al. | 320/118 |
| 2009/0112099 | A1 * | 4/2009 | Kurokawa | 600/459 |
| 2011/0043166 | A1 * | 2/2011 | Kawai et al. | 320/112 |

OTHER PUBLICATIONS

International Search Report (ISR) (PCT Form PCT/ISA/210) dated Oct. 4, 2011, in PCT/JP2011/070267.
International Preliminary Report on Patentability dated Mar. 14, 2013 and english translation thereof.
Extended European Search Report dated Jun. 12, 2017 in Patent Application No. PCT/JP2011070267.

* cited by examiner

ULTRASOUND DIAGNOSTIC EQUIPMENT WITH RECHARGEABLE ULTRASOUND PROBES

BACKGROUND OF THE INVENTION

The present invention relates to an ultrasound diagnostic equipment, in particular, an ultrasound diagnostic equipment in which a rechargeable ultrasound probe with a built-in battery and a diagnostic equipment body are connected together in a wireless manner.

An ultrasound diagnostic equipment using an ultrasound image has hitherto been put into practical use in the field of medicine. In general, this type of ultrasound diagnostic apparatus has an ultrasound probe with a built-in transducer array and a diagnostic equipment body connected to the ultrasound probe. In the ultrasound diagnostic apparatus, an ultrasonic wave is transmitted, from the ultrasound probe toward a subject, an ultrasonic echo from the subject is received by the ultrasound probe, and the reception signals are electrically processed in the diagnostic equipment body to produce an ultrasound image.

In recent years, an ultrasound diagnostic equipment has been developed in which the ultrasound probe and the diagnostic equipment body are connected through wireless communication in order to eliminate inconvenience of a communication cable which connects the ultrasound probe and the diagnostic equipment body, thereby improving operability. In this wireless ultrasound diagnostic equipment, for example, as described in JP 2003-10177 A, the ultrasound probe has a battery built-in as a power source, and when charging of the battery is required, power is supplied from a power supply unit of the diagnostic equipment body to the battery of the ultrasound probe in a noncontact manner through electromagnetic induction or the like in a state where the ultrasound probe is stored in a probe holder provided in the diagnostic equipment body.

In general, in a battery which is represented by a nickel-hydrogen battery or the like, if so-called top-up charging in which charging is performed before the residual amount of power of the battery becomes zero is frequently performed, it is noted that there is a problem in that the battery capacity is lowered due to the memory effect of the battery. In contrast with the top-up charging, if so-called refresh charging in which the battery is once discharged to make the residual amount of power zero and then charging is performed, is performed regularly, it is possible to extend the battery life.

However, since refresh charging takes a long period of time, the actual situation is that it is not easy to perform refresh charging of the battery built in to the ultrasound probe without causing a problem in an examination using the ultrasound diagnostic equipment.

SUMMARY OF THE INVENTION

The invention has been accomplished in order to solve the drawbacks in the prior art, and an object of the invention is to provide an ultrasound diagnostic equipment which is able to charge a battery of a rechargeable ultrasound probe while suppressing lowering in examination efficiency.

An ultrasound diagnostic equipment according to the present invention comprises at least one rechargeable ultrasound probe with a built-in battery, and a diagnostic equipment body connected to the at least one ultrasound probe in a wireless manner, wherein the diagnostic equipment body includes a power supply unit which supplies power to the battery of the at least one ultrasound probe, and a power supply controller which causes the battery of the at least one ultrasound probe to selectively perform refresh charging and top-up charging using the power supply unit on the basis of power supply information to the battery of the at least one ultrasound probe and the examination situation in the diagnostic equipment body.

DETAILED DESCRIPTION OF THE INVENTION

Hereinafter, embodiments of the invention will be described with reference to the accompanying drawings.

Embodiment 1

Figure 1:
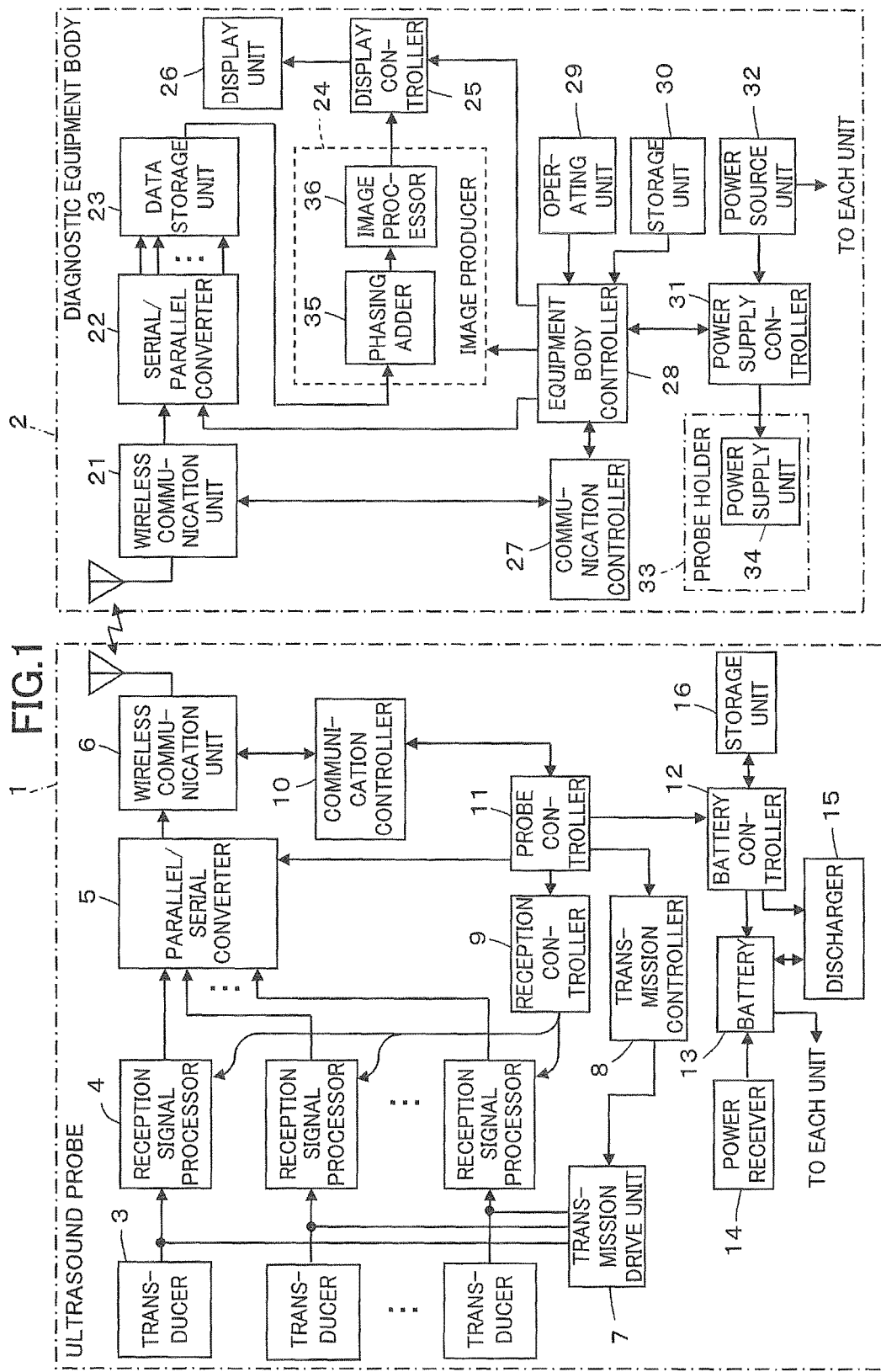
FIG. 1 is a block diagram illustrating the configuration of an ultrasound diagnostic equipment according to Embodiment 1 of the invention.

FIG. 1 illustrates the configuration of an ultrasound diagnostic equipment according to Embodiment 1 of the invention. The ultrasound diagnostic equipment includes a rechargeable ultrasound probe 1 and a diagnostic equipment body 2 connected to the ultrasound probe 1 through wireless communication.

The ultrasound probe 1 has a plurality of ultrasound transducers 3 which constitute a one-dimensional or two-dimensional transducer array. Reception signal processors 4 are correspondingly connected to the transducers 3, and a wireless communication unit 6 is connected to the reception signal processors 4 through a parallel/serial converter 5. A transmission controller 8 is connected to the plurality of transducers 3 through a transmission drive unit 7, a reception controller 9 is connected to the plurality of reception signal processors 4, and a communication controller 10 is connected to the wireless communication unit 6. A probe controller 11 is connected to the parallel/serial converter 5, the transmission controller 8, the reception controller 9, and the communication controller 10.

Moreover, a battery 13 is connected to the probe controller 11 through a battery controller 12, and a power receiver 14 for charging and a discharger 15 for discharging are connected to the battery 13, and the discharger 15 is connected to the battery controller 12. A storage unit 16 is connected to the battery controller 12.

Each of the plurality of transducers 3 transmits an ultrasonic wave in response to an actuation signal supplied from the transmission drive unit 7 and receives an ultrasonic echo from the subject, and outputs a reception signal. Each transducer 3 is constituted by a vibrator in which electrodes are formed at both ends of a piezoelectric body composed of, for example, piezoelectric ceramic represented by PZT (lead zirconate titanate), a polymer piezoelectric device represented by PVDF (polyvinylidene fluoride), or the like.

If a pulsed or continuous-wave voltage is applied across the electrodes of the vibrator, the piezoelectric body expands and contracts, whereby pulsed or continuous-wave ultrasonic waves are produced from the respective vibrators and the produced ultrasonic waves are synthesized to form an ultrasonic beam. When receiving propagating ultrasonic waves, the respective vibrators expand and contract to produce electric signals, and the electric signals are output as the reception signals of the ultrasonic waves.

The transmission drive unit 7 includes, for example, a plurality of pulse generators. The transmission drive unit 7 adjusts the delay amount of each of the actuation signals on the basis of a transmission delay pattern selected by the transmission controller 8 such that the ultrasonic waves transmitted from the plurality of transducers 3 form an ultrasonic beam having a width enough to cover the area of a tissue in the subject, and supplies the adjusted actuation signals to the plurality of transducers 3.

The reception signal processor 4 of each channel performs quadrature detection processing or quadrature sampling processing on the reception signal output from the corresponding transducer 3 under the control of the reception controller 9 to produce a complex baseband signal, samples the complex baseband signal to produce sample data including information on the area of the tissue, and supplies the sample data to the parallel/serial converter 5. The reception signal processor 4 may perform data compression processing for low bit rate coding on data obtained by sampling the complex baseband signal to produce sample data.

The parallel/serial converter 5 converts parallel sample data produced by the plurality of channels of reception signal processors 4 to serial sample data.

The wireless communication unit 6 modulates a carrier on the basis of the serial sample data to produce a transmission signal, supplies the transmission signal to an antenna, and transmits a radio wave from the antenna, thereby transmitting the serial sample data. As the modulation system, for example, ASK (Amplitude Shift Keying), PSK (Phase Shift Keying), QPSK (Quadrature Phase Shift Keying), 16QAM (16 Quadrature Amplitude Modulation), or the like is used.

The wireless communication unit 6 performs wireless communication with the diagnostic equipment body 2 to transmit the sample data to the diagnostic equipment body 2 and to receive various control signals from the diagnostic equipment body 2, and outputs the received control signals to the communication controller 10. The communication controller 10 controls the wireless communication unit 6 such that the sample data is transmitted with transmission radio field intensity set by the probe controller 11, and outputs various control signals received by the wireless communication unit 6 to the probe controller 11.

The probe controller 11 controls the respective units of the ultrasound probe 1 on the basis of various control signals transmitted from the diagnostic apparatus body 2.

The battery 13 functions as a power source of the ultrasound probe 1, and supplies power to the respective units, which require power, in the ultrasound probe 1. The battery controller 12 controls power supply from the battery 13 to the respective units in the ultrasound probe 1, monitors the residual amount of power of the battery 13, and each time the battery 13 is charged through the power receiver 14, updates the number of times of charging and stores the number of times of charging updated in the storage unit 16. Though described below, since the number of times of charging of the battery 13 stored in the storage unit 16 is reset to zero when refresh charging is executed, the number of times of successions of top-up charging is stored in the storage unit 16. The discharger 15 discharges the battery 13 on the basis of an instruction from the battery controller 12, and makes the residual amount of power zero.

The ultrasound probe 1 may be an external probe, such as a linear scan type, a convex scan type, or a sector scan type, or may be a probe for an ultrasound endoscope, such as a radial scan type.

The diagnostic equipment body 2 has a wireless communication unit 21. A data storage unit 23 is connected to the wireless communication unit 21 through a serial/parallel converter 22, and an image producer 24 is connected to the data storage unit 23. A display unit 26 is connected to the image producer 24 through a display controller 25. A communication controller 27 is connected to the wireless communication unit 21, and an equipment body controller 28 is connected to the serial/parallel converter 22, the image producer 24, the display controller 25, and the communication controller 27. An operating unit 29 for an input operation by an operator and a storage unit 30 which stores operation programs are respectively connected to the equipment body controller 28.

Further, a power source unit 32 is connected to the equipment body controller 28 through a power supply controller 31. A probe holder 33 which holds the ultrasound probe 1 not in use is formed in the diagnostic equipment body 2, and a power supply unit 34 is provided in the probe holder 33.

The wireless communication unit 21 performs wireless communication with the ultrasound probe 1 to transmit various control signals to the ultrasound probe 1. Besides, the wireless communication unit 21 demodulates a signal received by an antenna to output serial sample data.

The communication controller 27 controls the wireless communication unit 21 such that various control signals are transmitted with transmission radio field intensity set by the equipment body controller 28.

The serial/parallel converter 22 converts the serial sample data output from the wireless communication unit 21 to parallel sample data. The data storage unit 23 is constituted by a memory, a hard disk, or the like, and stores the sample data for at least one frame converted by the serial/parallel converter 22.

The image producer 24 performs reception focus processing on the sample data for every frame read from the data storage unit 23 to produce an image signal representing an ultrasound diagnostic image. The image producer 24 includes a phasing adder 35 and an image processor 36.

The phasing adder 35 performs the reception focus processing by selecting one reception delay pattern from among a plurality of reception delay patterns stored in advance in accordance with a reception direction set in the equipment body controller 28, giving a delay to each of a plurality of complex baseband signals represented by the sample data on the basis of the selected reception delay pattern, and adding the reception signals. With this reception focus processing, the focus of the ultrasonic echo is narrowed to produce a baseband signal (sound ray signal).

The image processor 36 produces a B-mode image signal, which is tomographic image information relating to a tissue in the subject, on the basis of the sound ray signal produced by the phasing adder 35. The image processor 36 includes an STC (sensitivity time control) unit and a DSC (digital scan converter). The STC unit corrects attenuation depending on the distance in accordance with the depth of the reflection position of the ultrasonic wave for the sound ray signal. The DSC converts (raster-converts) the sound ray signal corrected by the STC unit to an image signal based on a normal television signal scan system, and performs necessary image processing, such as gradation processing, to produce a B-mode image signal.

The display controller 25 displays an ultrasound diagnostic image on the display unit 26 on the basis of the image signal produced by the image producer 24. The display unit 26 includes, for example, a display device, such as an LCD, and displays the ultrasound diagnostic image under the control of the display controller 25.

The equipment body controller 28 controls the respective units in the diagnostic equipment body 2.

The power source unit 32 supplies power to the respective units, which require power, in the diagnostic equipment body 2. The power supply controller 31 connects the power source unit 32 to the power supply unit 34 of the probe holder 33 as necessary on the basis of the examination situation in the diagnostic equipment body 2 input through the equipment body controller 28 and power supply information, such as the residual amount of power and the number of times of charging of the battery 13 transmitted from the ultrasound probe 1 through wireless communication, and causes the battery 13 of the ultrasound probe 1 to selectively perform refresh charging and top-up charging. The power supply unit 34 of the probe holder 33 supplies power to the power receiver 14 of the ultrasound probe 1 held in the probe holder 33 in a noncontact manner through electromagnetic induction or the like.

Although in the diagnostic equipment body 2, the serial/parallel converter 22, the image producer 24, the display controller 25, the communication controller 27, the equipment body controller 28, and the power supply controller 31 are constituted by a CPU and operation programs which cause the CPU to perform various types of processing, these may be constituted by digital circuits. The operation programs are stored in the storage unit 30. As a recording medium in the storage unit 30, in addition to an internal hard disk, a flexible disk, an MO, an MT, a RAM, a CD-ROM, a DVD-ROM, or the like may be used.

During diagnosis, first, ultrasonic waves are transmitted from the plurality of transducers 3 in accordance with the actuation signals supplied from the transmission drive unit 7 of the ultrasound probe 1, and the reception signal output from each transducer 3 having received the ultrasonic echo from the subject is supplied to the corresponding reception signal processor 4 to produce sample data. The sample data is converted to serial sample data by the parallel/serial converter 5, and the serial sample data is transmitted from the wireless communication unit 6 to the diagnostic equipment body 2 in a wireless manner. The sample data received by the wireless communication unit 21 of the diagnostic equipment body 2 is converted to parallel sample data by the serial/parallel converter 22, and the parallel sample data is stored in the data storage unit 23. The sample data for every frame is read from the data storage unit 23, an image signal is produced by the image producer 24, and an ultrasound diagnostic image is displayed on the display unit 26 on the basis of the image signal by the display controller 25.

Ultrasound diagnosis is performed in this way, and in the ultrasound probe 1, the residual amount of power of the battery 13 is monitored by the battery controller 12 and the number of times of charging of the battery 13 is stored in the storage unit 16. The power supply controller 31 of the diagnostic equipment body 2 can recognize the residual amount of power and the number of times of charging of the battery 13 through the equipment body controller 28 and the communication controller 27 by wireless communication. Further, the power supply controller 31 can recognize the examination situation in the diagnostic equipment body 2 through the equipment body controller 28. When the ultrasound probe 1 is not used, the ultrasound probe 1 is held in the probe holder 33 of the diagnostic equipment body 2.

Figure 2:
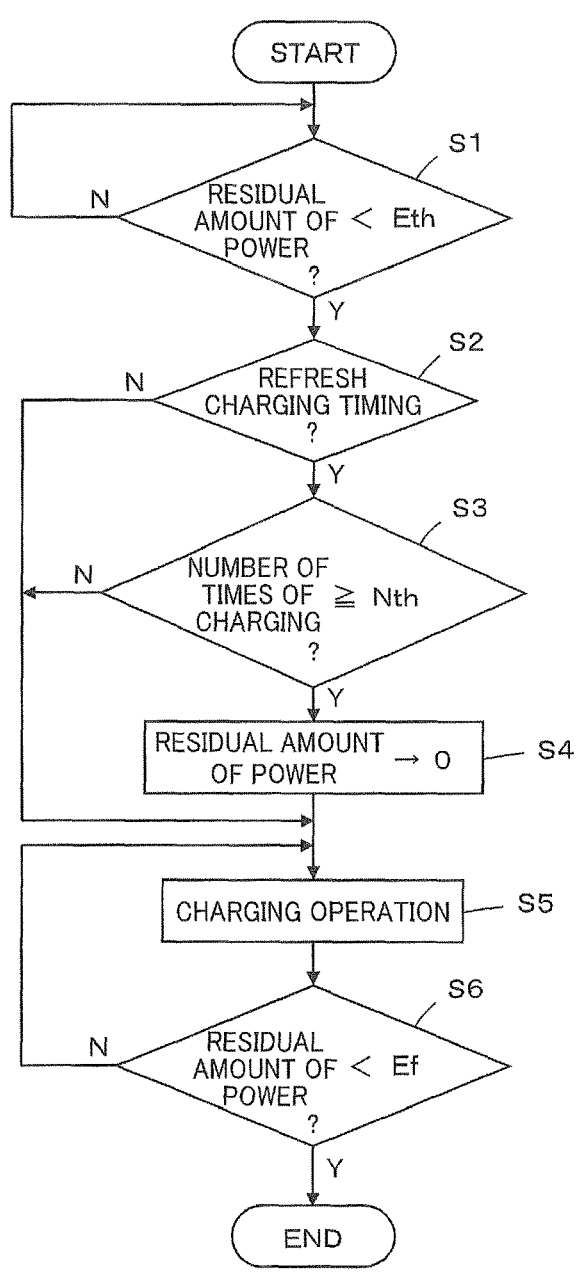
FIG. 2 is a flowchart illustrating an operation of a power supply controller in Embodiment 1.

Here, the operation of the power supply controller 31 of the diagnostic equipment body 2 will be described with reference to the flowchart of FIG. 2.

First, in Step S1, the residual amount of power of the battery 13 is compared with a threshold value Eth set in advance. The threshold value Eth is used to decide whether or not it is necessary to charge the battery 13. If it is determined that the residual amount of power of the battery 13 falls below the threshold value Eth, the process progresses to Step S2, and it is determined whether or not it is a refresh charging timing from the examination situation in the diagnostic equipment body 2.

In general, since refresh charging requires a long period of time, the timing at which it is foreseen that the ultrasound probe 1 is held in the probe holder 33 of the diagnostic apparatus body 2 over a predetermined time or more is detected as the refresh charging timing, and the examples of the timing include the cases where the examination for the day ends, a long vacant time is secured in the intervals between examinations, and the like.

If it is determined in Step S2 that it is the refresh charging timing, in Step S3, it is further determined whether or not the number of times of charging of the battery 13 stored in the storage unit 16 of the ultrasound probe 1 reaches a predetermined threshold value Nth, for example, ten times. As described above, since the number of times of charging stored in the storage unit 16 of the ultrasound probe 1 represents the number of successions of top-up charging of the battery 13, it is decided whether or not top-up charging of the battery 13 is performed successively, for example, ten times or more.

If it is determined in Step S3 that the number of times of charging of the battery 13 has reached the threshold value Nth, it is judged that refresh charging should be executed, and in Step S4, the battery 13 is discharged once by the discharger 15 through the battery controller 12 of the ultrasound probe 1 to make the residual amount of power zero. Thereafter, in Step S5, power is supplied from the power supply unit 34 of the probe holder 33 to the power receiver 14 of the ultrasound probe 1 held in the probe holder 33 in a noncontact manner through electromagnetic induction or the like, and the charging operation of the battery 13 is executed. The charging operation is continued until the residual amount of power of the battery 13 becomes a maximum value Ef representing full charging completion in the next Step S6. Thereby, refresh charging of the battery 13 is completed.

If refresh charging is completed in this way, the number of times of charging stored in the storage unit 16 is reset to zero by the battery controller 12 of the ultrasound probe 1.

When it is determined in Step S2 that it is not the refresh charging timing and when it is determined in Step S3 that the number of times of charging of the battery 13 has not reached the threshold value Nth, it is judged that refresh charging should be not executed. In this case, the battery 13 is not discharged in Step S4, the process progresses to Step S5 directly, and the charging operation is performed. That is, top-up charging is executed.

In this case, the number of times of charging stored in the storage unit 16 is incremented by "1" by the battery controller 12 of the ultrasound probe 1.

As described above, according to Embodiment 1, when it is necessary to charge the battery 13 of the ultrasound probe 1, the power supply controller 31 of the diagnostic equipment body 2 causes the battery 13 of the ultrasound probe 1 to selectively perform refresh charging and top-up charging by the power supply unit 34 of the probe holder 33 on the basis of the power supply information to the battery 13 and the examination situation in the diagnostic apparatus body 2. Therefore, it becomes possible to charge the battery 13 of the ultrasound probe 1 while suppressing lowering in examination efficiency.

Although in Embodiment 1, the power supply controller 31 of the diagnostic equipment body 2 determines whether or not to perform refresh charging on the basis of the power supply information to the battery 13 and the examination situation in the diagnostic equipment body 2, a confirmation screen of refresh charging may be displayed on the display unit 26 of the diagnostic equipment body 2, and the operator may input an instruction for refresh charging while viewing the confirmation screen. For example, during shutdown of the equipment, a screen illustrated in FIG. 3 may be displayed, and one of buttons for refresh charging, shutdown, and cancel may be selected, or during standby of the equipment, a screen illustrated in FIG. 4 may be displayed, and one of buttons for refresh charging, standby, and cancel may be selected. When the button for refresh charging is selected, a screen illustrated in FIG. 5 may be displayed, and a button for execute charging may be selected to start the execution of refresh charging.

Figure 3:
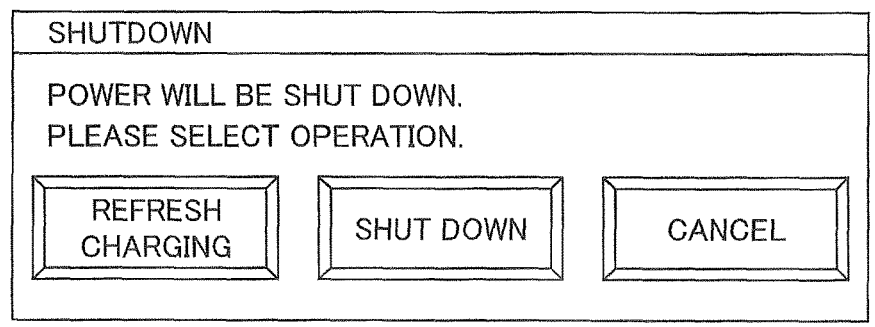
FIG. 3 is a diagram illustrating screen display during shutdown in a modification of Embodiment 1.
Figure 4:
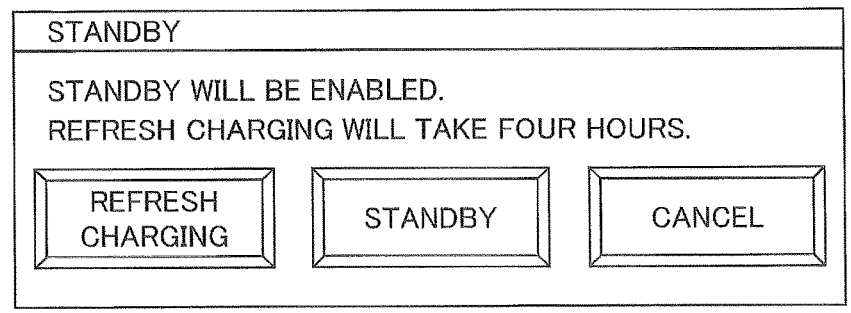
FIG. 4 is a diagram illustrating screen display during standby in the modification of Embodiment 1.
Figure 5:
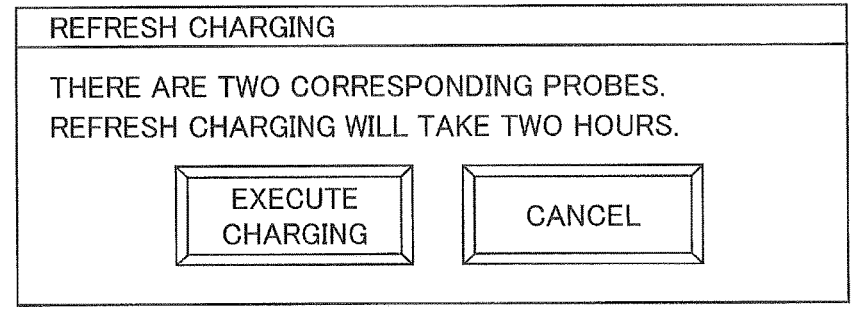
FIG. 5 is a diagram illustrating screen display during refresh charging in the modification of Embodiment 1.

Even when the power supply controller 31 of the diagnostic equipment body 2 determines that refresh charging should not be executed on the basis of the power supply information to the battery 13 and the examination situation in the diagnostic equipment body 2, a screen illustrated in FIG. 3 or 4 may be displayed, and the button for refresh charging may be grayed out to be not selectable, or only the button for refresh charging may not be displayed.

Even when the button of the equipment is long pressed to turn off power, for example, when the equipment will be restarted due to starting failure, or the like, it is possible to set whether or not to perform refresh charging.

Further, even in the case where refresh charging is executed when the equipment is shutdown, the ultrasound diagnostic equipment may be constituted such that the ultrasound diagnostic equipment is started as necessary in the midstream of charging.

Although in Embodiment 1, in Step S1 of FIG. 2, when it is determined that the residual amount of power of the battery 13 falls below the threshold value Eth set in advance, refresh charging or top-up charging is performed, in regard to top-up charging, the charging operation may be performed each time the ultrasound probe 1 is held in the probe holder 33.

Although in Step S4, the battery 13 is discharged by the discharger 15 through the battery controller 12 of the ultrasound probe 1, the invention is not limited thereto, and a battery discharging coil may be arranged in the probe holder 33 of the diagnostic equipment body 2 in advance, and the battery discharging coil may be driven to discharge the battery 13 of the ultrasound probe 1 held in the probe holder 33.

Embodiment 2

Figure 6:
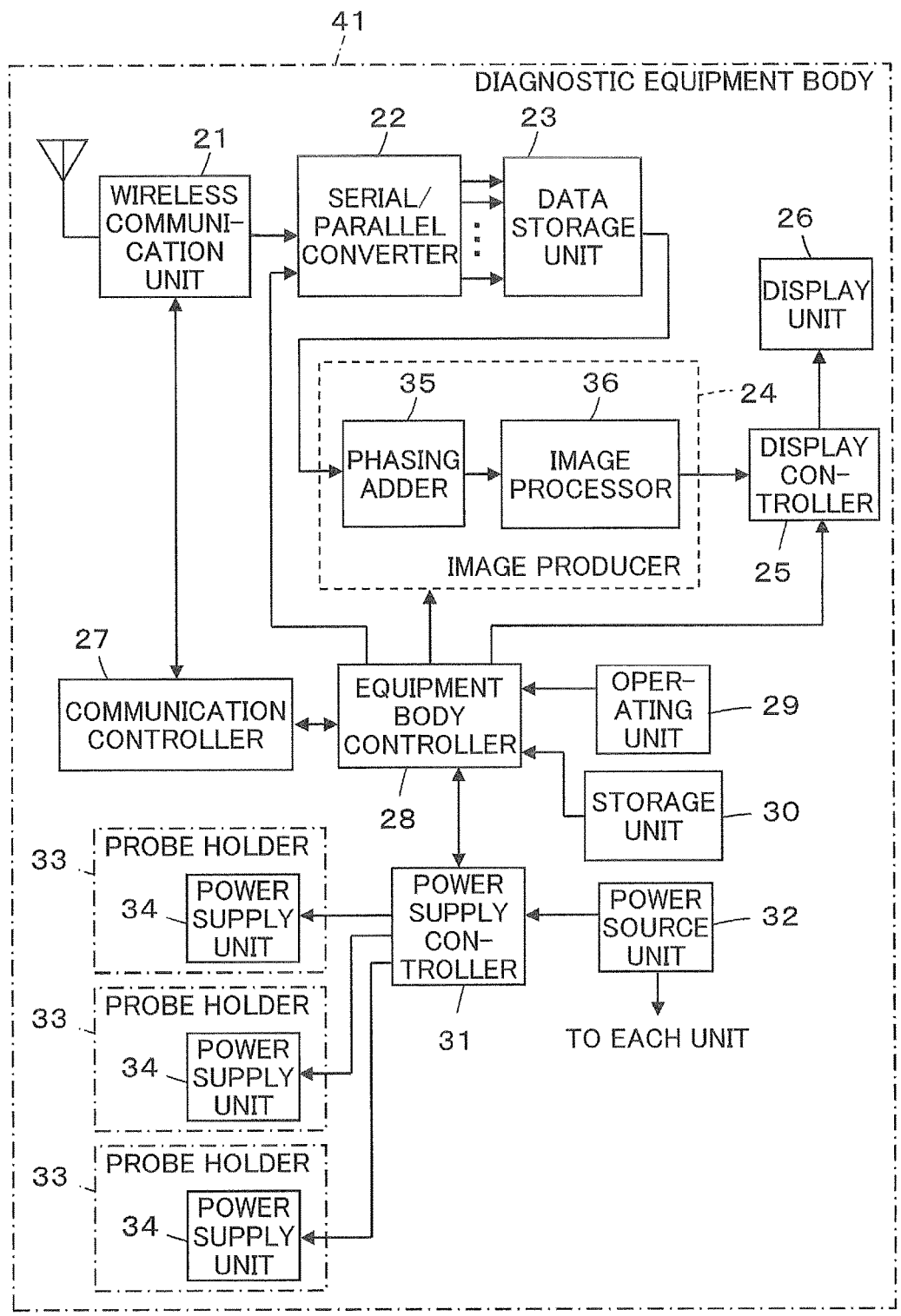
FIG. 6 is a block diagram illustrating the configuration of a diagnostic equipment body used in an ultrasound diagnostic equipment according to Embodiment 2.

FIG. 6 illustrates the configuration of a diagnostic equipment body 41 used in an ultrasound diagnostic equipment according to Embodiment 2. The diagnostic equipment body 41 includes a plurality of probe holders 33 each having the power supply unit 34, and each power supply unit 34 is connected to the power supply controller 31. Other parts are the same as the diagnostic equipment body 2 in Embodiment 1 illustrated in FIG. 1.

In general, in ultrasound diagnosis, an appropriate ultrasound probe is selected in accordance with a region to be examined, the body shape of the subject, or the like. A scanning mode probe corresponding to a region to be examined may be used, or a probe having a different width due to a difference in an examination purpose may be selected for the same region to be examined. If an ultrasound probe is selected once and scanning starts, rarely switched to any of other ultrasound probes often to perform scanning, and even when candidates of a plurality of ultrasound probes are extracted prior to an examination, the ultrasound probes other than an ultrasound probe to be actually used can continue to be charged.

Accordingly, in the ultrasound diagnostic equipment according to Embodiment 2, the plurality of probe holders 33 are provided in the diagnostic equipment body 41, and a plurality of ultrasound probes 1 can be respectively held in the probe holders 33. The residual amount of power and the number of times of charging of the battery 13 of the ultrasound probe 1, and the use situation of the ultrasound probe 1 differ between the respective ultrasound probes 1. For this reason, for the plurality of ultrasound probes 1 held in the plurality of probe holders 33, the power supply controller 31 of the diagnostic equipment body 41 performs the determination of the residual amount of power, the determination of the refresh charging timing, and the determination of the number of times of charging with respect to each battery 13 as illustrated in the flowchart of FIG. 2, thereby as necessary, causing each battery 13 of the ultrasound probes 1 to selectively perform refresh charging and top-up charging using the power supply unit 34 of the respective probe holder 33.

At this time, the power supply controller 31 may determine whether or not refresh charging is possible in the batteries 13 of the ultrasound probes 1 on the basis of the types of the plurality of ultrasound probes 1 held in the plurality of probe holders 33 and the power supply information corresponding to the batteries 13 of the plurality of ultrasound probes 1.

When a plurality of ultrasound probes 1 of the same type are used, it is possible to prevent simultaneous refresh charging in all of the plurality of ultrasound probes 1. For example, when two linear scan type probes are used together and if refresh charging is in midstream for one linear scan type probe, in regard to the other one linear scan type probe, even when the number of times of charging of the battery 13 exceeds the threshold value Nth, it is regulated such that refresh charging is not performed.

Specifically, even when it is recognized on the basis of the power supply information received from the ultrasound probe 1 that a further ultrasound probe 1 of the same type is set in an empty probe holder 33 of the diagnostic equipment body 41, refresh charging is not permitted to start for the battery 13 of the ultrasound probe 1 set. Meanwhile, top-up charging is permitted. Accordingly, refresh charging is not performed for all of the necessary ultrasound probes 1 simultaneously, whereby it is possible to cope with an abrupt request to use an ultrasound diagnostic equipment. When refresh charging does not start for the battery 13 of the ultrasound probe 1 set in the probe holder 33, display to the effect that refresh charging is not performed tentatively may be performed.

The power supply controller 31 may designate the ultrasound probe 1, in which refresh charging is preferentially performed, from among a plurality of ultrasound probes 1 held in the plurality of probe holders 33 on the basis of the power supply information corresponding to the batteries 13 of the plurality of ultrasound probes 1.

When there is a plurality of ultrasound probes 1 in which the number of times of charging of the battery 13 has reached the predetermined threshold value Nth, refresh charging of the battery 13 of the ultrasound probe 1 is performed in a descending order of the number of times of charging. For example, in regard to three ultrasound probes A to C, when the number of times of charging of the battery 13 of the ultrasound probe A is 20, the number of times of charging of the battery 13 of the ultrasound probe B is 15, and the number of times of charging of the battery 13 of the ultrasound probe C is 12, the power supply controller 31 issues an instruction to each power supply unit 34 such that refresh charging is preferentially performed in a descending order of the number of times of charging, that is, in an order of the ultrasound probe A, the ultrasound probe B, and the ultrasound probe C. Accordingly, the ultrasound probe 1 in which refresh charging will be required is preferentially designated, thereby achieving improvement in operability.

Further, the power supply controller 31 may designate the ultrasound probe 1, in which refresh charging is preferentially performed, from among a plurality of ultrasound probes 1 on the basis of the previous examination situations of the battery 13 corresponding to the plurality of ultrasound probes 1 held in a plurality of probe holders 33.

When a plurality of ultrasound probes 1 in which the number of times of charging of the battery 13 has reached the predetermined threshold value Nth, refresh charging of the battery 13 of the ultrasound probe 1 is performed in a descending order of use frequency on the basis of the examination situation representing history information of each ultrasound probe 1. For example, in regard to three ultrasound probes A to C, the power supply controller 31 issues an instruction to each power supply unit 34 such that refresh charging is preferentially performed in an order of the ultrasound probe A, the ultrasound probe B, and the ultrasound probe C. Accordingly, the ultrasound probe 1 having the highest use frequency is preferentially designated from among the ultrasound probes 1 in which refresh charging will be required, thereby achieving improvement in operability.

In this way, a plurality of ultrasound probes 1 corresponding to various diagnosis purposes selectively perform refresh charging and top-up charging depending on the residual amount of power of the battery, the number of times of charging of the battery, and the use situation, making it possible to charge the battery 13 of the ultrasound probe 1 while suppressing lowering in examination efficiency of ultrasound diagnosis.

Although in the foregoing embodiments, an example where the number of times of charging of the battery 13 is stored as information stored in the storage unit 16 has been described, not only the number of times of charging of the battery 13, but also the residual amount of power of the battery 13 monitored by the battery controller 12 may be stored.

Examples 1 to 7 relating to the flow of an examination of specific ultrasound diagnosis and the timing at which top-up charging and refresh charging are performed will be described below.

Operation of various buttons in Examples 1 to 7 is made through the operating unit 29. On the basis of an instruction input to the operating unit 29, the examination situation in the power supply controller 31 is determined through the equipment body controller 28.

Example 1

[A Case where the Result Report, Charting, and the Like are Made After Image Diagnosis is First Performed]

An examination is performed along Steps 1 to 8.

1. A patient information input button "New Patient" is pressed.

2. A screen for inputting patient information is displayed and patient information is input.

3. An "Exit" button is pressed to start the examination.

4. Scanning by the ultrasound probe is performed.

5. An "End Exam" button is pressed to end the examination.

6. The result report or the like is made.

7. Explanation to the patient and charting are made.

8. The next patient is called and the "New Patient" button is pressed.

Since the ultrasound probe is not used and is held in the probe holder during Steps 6 to 8, top-up charging can be performed.

Example 2

[A Case where a Patient Input is Performed to Make a Medical Inquiry, and Image Diagnosis is Performed]

An examination is performed along Steps 1 to 14.

1. The patient information input button "New Patient" is pressed.

2. A screen for inputting patient information is displayed and patient information is input.

3. The "Exit" button is pressed to start the examination.

4. A "Freeze" button is pressed to start a medical inquiry. At this time, an aerial emission state from the ultrasound probe may be detected, and freeze may be automatically made.

5. The patient makes preparations, such as change of clothes, so as to receive an examination.

6. The patient notifies a physician or technician that the preparations are completed.

7. The "Freeze" button is pressed again to release freeze.

8. Scanning by the ultrasound probe is performed.

9. The "End Exam" button is pressed to end the examination.

10. The "Freeze" button is pressed to make freeze. The setting may be made such that the freeze state is reached after the "End Exam" button is pressed. An aerial emission state from the ultrasound probe may be detected, and freeze may be automatically made.

11. It waits until the change of clothes or the like of the patient is completed.

12. The result report or the like is made.

13. Explanation to the patient and charting are made.

14. The next patient is called and "New Patient" is pressed.

In Steps 4 to 7 and Steps 10 to 14, since the ultrasound probe is not used and is held in the probe holder, top-up charging can be performed.

Example 3

[A Case where an Examination List is Called Up from an Electronic Chart System or the Like and Operated]

An examination is performed along Steps 1 to 10.
1. The patient information input button "New Patient" is pressed.
2. A screen for inputting patient information is displayed and patient information is input.
3. A "Worklist" button is pressed to call up the chart of the patient to be examined, and the "Exit" button is pressed to progress an examination screen.
4. The "Freeze" button is pressed, the patient is called, and a previous result report, a medical inquiry, or the like is made.
5. The patient makes preparations, such as change of clothes, so as to receive an examination.
6. The "Freeze" button is pressed again to release freeze.
7. Scanning by the ultrasound probe is performed.
8. The "End Exam" button is pressed to end the examination.
9. Explanation to the patient and charting are made.
10. The patient information input button "New Patient" is pressed for the next patient.

Since the ultrasound probe is not used and is held in the probe holder during Steps 1 to 6 and Steps 9 to 10, top-up charging can be performed.

Example 4

[A Case where an Examination Starts in Emergency or First Aid Without Inputting Patient Information]

An examination is performed along Steps 1 to 2.
1. Scanning by the ultrasound probe is performed.
2. The "End Exam" button is pressed to end the examination. When an examination is performed without inputting patient information in this way, this means first aid and, therefore, charging of the battery of the ultrasound probe is cancelled during the flow of the examination. When it is assumed that many patients are coming, and the frequency that the ultrasound probe returns to the probe holder is small, the setting may be made such that top-up charging is performed each time the ultrasound probe returns to the probe holder.

Example 5

[A Case where a Preset Examination is Selected in Emergency or First Aid]

An examination is performed along Steps 1 to 3.
1. A preset for first aid or emergency is selected.
2. Scanning by the ultrasound probe is performed.
3. The "End Exam" button is pressed to end the examination.

In the preset for first aid or emergency, charging to the battery of the ultrasound probe is cancelled during the flow of the examination. However, since a certain level of frequency that the ultrasound probe returns to the probe holder is expected, when the residual amount of power of the battery falls below a threshold value Eth, the setting may be made such that top-up charging is performed each time the ultrasound probe returns to the probe holder. When a preset other than for a first aid and emergency is selected, the charging method may be automatically switched to the charging method illustrated in FIG. 2.

Example 6

[A Case where an Ultrasound Probe to be Used Differs Depending on a Region to be Examined, and the Result Report, Charting, and the Like are Made after Image Diagnosis is First Performed]

An examination is performed along Steps 1 to 8.
1. The patient information input button "New Patient" is pressed.
2. A screen for inputting patient information is displayed and patient information is input.
3. The "Exit" button is pressed to start the examination. Here, the first ultrasound probe which is used for the examination is selected.
4. Scanning by the first ultrasound probe is performed.
5. The "End Exam" button is pressed to end the examination.
6. The result report or the like is made.
7. Explanation to the patient and charting are made.
8. The next patient is called and the "New Patient" button is pressed.

In Steps 6 to 8, since the first ultrasound probe is not used and is held in the probe holder, top-up charging can be performed to the first ultrasound probe. In regard to the ultrasound probes other than the first ultrasound probe, top-up charging and refresh charging can continue until each ultrasound probe is selected for use, including Steps 3 to 8.

Example 7

[A Case where Two or More Types of Ultrasound Probes are Used During an Examination, and the Result Report, Charting, and the Like are Made after Image Diagnosis is First Performed]

An examination is performed along Steps 1 to 8.
1. The patient information input button "New Patient" is pressed.
2. A screen for inputting patient information is displayed and patient information is input.
3. The "Exit" button is pressed to start the examination. Here, the first ultrasound probe to be first used is selected.
4. Scanning by the first ultrasound probe is performed.
5. The second ultrasound probe to be next used is selected.
6. The operation of the first ultrasound probe is temporarily stopped.
7. Scanning by the second ultrasound probe is performed.
8. The "End Exam" button is pressed to end the examination.
9. The result report or the like is made.
10. Explanation to the patient and charting are made.
11. The next patient is called and the "New Patient" button is pressed.

In regard to the first ultrasound probe, top-up charging may be performed during Steps 6 to 11, and in regard to the second ultrasound probe, top-up charging may be performed during Steps 1 to 5 and during Steps 9 to 11.

What is claimed is:
1. An ultrasound diagnostic equipment comprising:
a plurality of rechargeable ultrasound probes, the plurality of rechargeable ultrasound probes comprising a first rechargeable ultrasound probe comprising a first battery and a second rechargeable ultrasound probe comprising a second battery; and
a diagnostic equipment body connected to the plurality of ultrasound probes in a wireless manner, wherein the diagnostic equipment body includes
a plurality of probe holders configured to hold the plurality of rechargeable ultrasound probes,
a power source unit configured to supply power to the first and second batteries; and
a power supply controller configured to:
   determine whether or not it is necessary to charge the first battery based whether or not a residual amount of power of the first battery falls below a first threshold value,
   determine whether or not it is a refresh charging timings wherein the refresh charging timing is a timing of an end of an examination for the day, at which the first battery is to be once discharged to make the residual amount of power of the first battery zero and then is to be charged,
   determines whether a number of times of top-up charging of the first battery has reached a predetermined second threshold value,
   perform a refresh charging of the first battery using the power source unit in a case of determining that it is necessary to charge the first battery, that it is the refresh charging timing and that the number of times of top-up charging of the first battery has reached the predetermined second threshold value, and reset the number of times of top-up charging of the first battery to zero when the refresh charging of the first battery is completed,
   perform a top-up charging of the first battery using the power source unit in a case of determining that it is necessary to charge the first battery and that it is not the refresh charging timing, and
   perform a top-up charging of the first battery using the power source unit in a case of determining that it is necessary to charge the first battery, that it is the refresh charging timing and that the number of times of top-up charging of the first battery has not reached the predetermined second threshold value:
wherein the power supply controller is further configured to:
   determine whether or not it is necessary to charge the second battery while the refresh charging of the first battery is being performed based on whether or not a residual amount of power of the second battery falls below the first threshold value,
   determine whether or not the first rechargeable ultrasound probe has an identical type with that of the second rechargeable ultrasound probe, and
   if the first and second rechargeable ultrasound probes have the identical type and if it is necessary to charge the second battery while the refresh charging of the first battery is being performed, perform a top-up charging of the second battery using the power source unit without performing a refresh charging of the second battery.

2. The ultrasound diagnostic equipment according to claim 1,
   wherein the ultrasound diagnostic equipment comprises a storage unit which stores the residual amount of power of each of the first battery and the second battery and the number of times of top-up charging of each of first battery and the second battery.

3. The ultrasound diagnostic equipment according to claim 1,
   wherein the power supply controller is configured to, if it is determined that it is necessary to charge a both the first battery and the second battery, that it is the refresh charging timing and that both the number of times of top-up charging of the first battery and the number of times of top-up charging of the second battery reached the predetermined second threshold value, perform the refresh charging of one of the first battery and the second battery having a larger number of times of top-up charging.

4. The ultrasound diagnostic equipment according to claim 1,
   wherein the power supply controller is configured to:
      if the residual amount of power of the first battery is equal to or larger than the first threshold value, preclude the refresh charging of the first battery and preclude the top-up charging of the first battery, and
      if the residual amount of power of the second battery is equal to or larger than the first threshold value, preclude the refresh charging of the second battery and preclude the top-up charging of the second battery.

* * * * *